(12) United States Patent
Burstein et al.

(10) Patent No.: US 6,974,835 B2
(45) Date of Patent: Dec. 13, 2005

(54) METHODS FOR DECREASING CELL PROLIFERATION BASED ON (3R,4R)-Δ8-TETRAHYDROCANNABINOL-11-OIC ACIDS

(75) Inventors: Sumner Burstein, Farmington, MA (US); Lawrence Recht, Holden, MA (US); Robert B. Zurier, Princeton, MA (US)

(73) Assignee: Indevus Pharmaceuticals, Inc., Lexington, MA (US)

( * ) Notice: Subject to any disclaimer, the term of this patent is extended or adjusted under 35 U.S.C. 154(b) by 53 days.

(21) Appl. No.: 10/276,818

(22) PCT Filed: May 17, 2001

(86) PCT No.: PCT/US01/15916

§ 371 (c)(1),
(2), (4) Date: Sep. 17, 2003

(87) PCT Pub. No.: WO01/87295

PCT Pub. Date: Nov. 22, 2001

(65) Prior Publication Data

US 2004/0054007 A1 Mar. 18, 2004

Related U.S. Application Data

(60) Provisional application No. 60/204,935, filed on May 17, 2000.

(51) Int. Cl.$^7$ .............................................. A61K 31/19
(52) U.S. Cl. ................................................... 514/570
(58) Field of Search ........................... 514/568, 298, 514/454, 570

(56) References Cited

U.S. PATENT DOCUMENTS 6,274,635 B1 * 8/2001 Travis ........................ 514/718

OTHER PUBLICATIONS

Cecil, Textbook of Medicine, 21$^{st}$ Edition, vol. 1, Goldman et al. (eds.), published 2000 by WB Saunders Co. (PA) pp 1060–1073.*

* cited by examiner

*Primary Examiner*—Raymond J. Henley, III
(74) *Attorney, Agent, or Firm*—Muchin Rosenman LLP; Gilberto M. Villacorta; Robert W. Hahl

(57) ABSTRACT

The invention relates to the use of cannabinoid compounds (derivatives of tetrahydrocannabinol) for decreasing cell proliferation in a mammal.

13 Claims, 2 Drawing Sheets

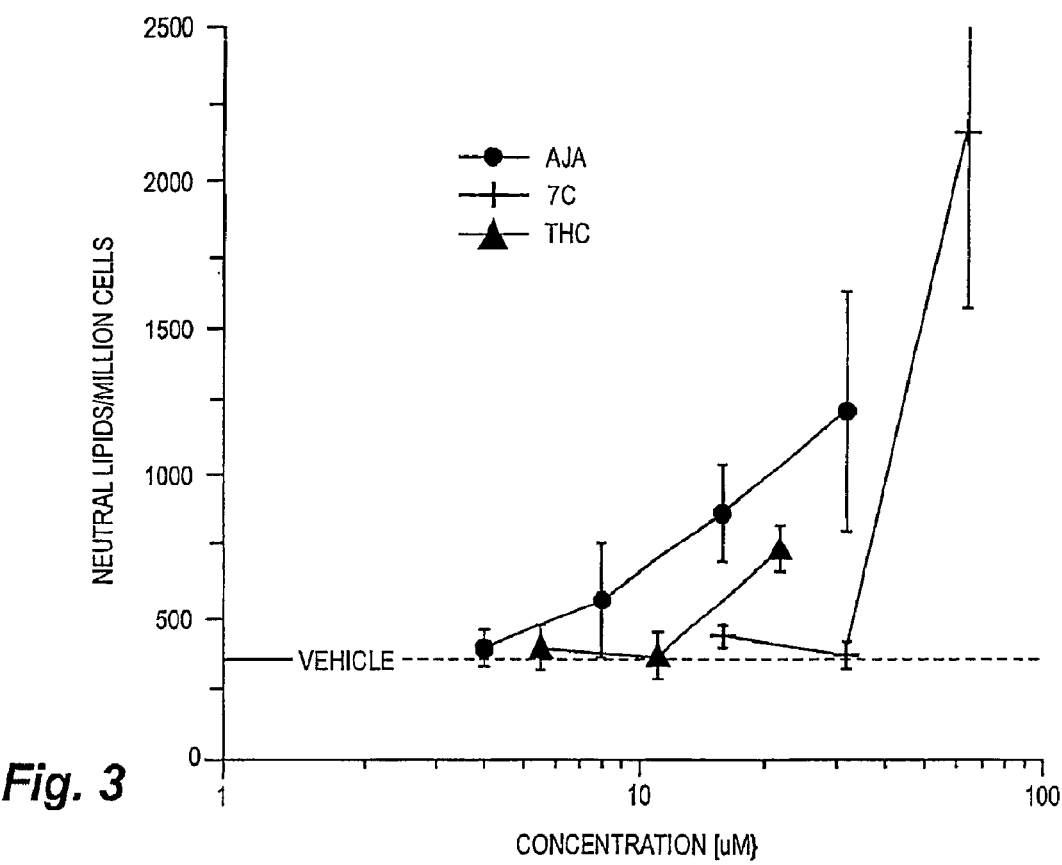
Fig. 3
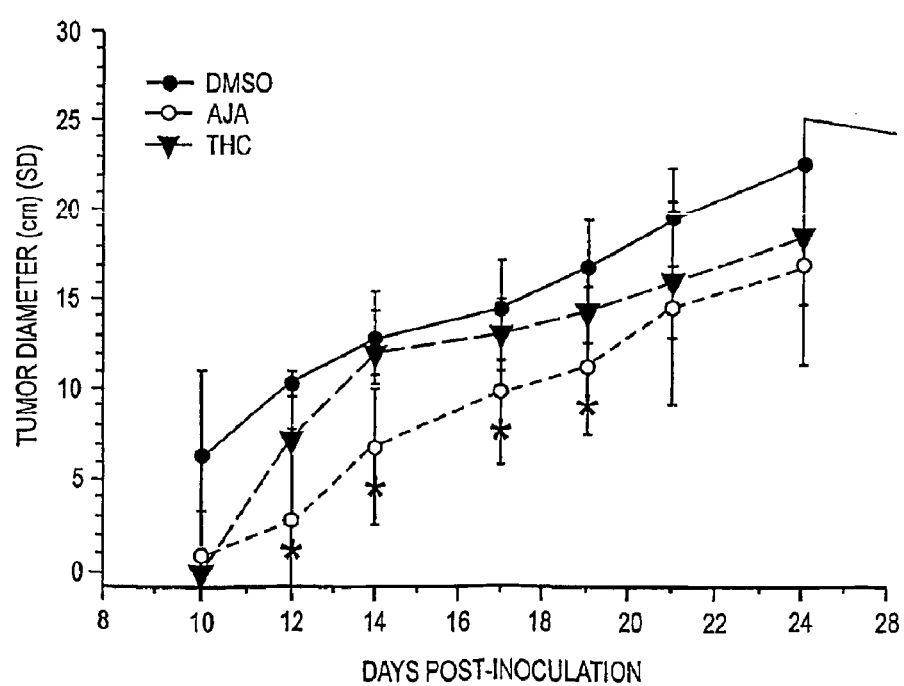
Fig. 4    *P<0.05, DUNNETT'S TEST VS BOTH THC AND DMSO

METHODS FOR DECREASING CELL PROLIFERATION BASED ON (3R,4R)-Δ8-TETRAHYDROCANNABINOL-11-OIC ACIDS This application is a 371 of PCT/US01/15916, filed May 17, 2001, which claims the benefit of U.S. Provisional Application No. 60/204,935, filed May 17, 2000.

FIELD OF THE INVENTION

This invention relates to cancer therapy and organic chemistry.

BACKGROUND OF THE INVENTION

The psychoactive agent in Cannabis plant material is tetrahydrocannabinol (THC). Since THC is known to elicit various physiological effects (e.g., as an anti-inflammatory agent or analgesic) other than psychoactivity, various derivatives of THC that retain a favorable biochemical or pharmacological activity of THC without any potential for abuse or psychoactivity are beneficial and have been synthesized as potential drugs.

One of the activities associated with THC and some of its derivatives is inhibition of cell proliferation. However, this activity, as with psychoactivity, is dependent on binding to the cannabinoid receptor CB1 (Galve-Roperh et al., Nat. Med. 6:313–319, 2000; De Petrocellis et al., Proc. Natl. Acad. Sci. USA 95:8375–8380, 1998; and Bisogno et al., Eur. J. Biochem. 254:634–642, 1998). Thus, non-psychoactive derivatives of THC, which do not bind to the CB1 receptor (Burstein, Pharmacol. Ther. 82:87–96, 1999), are not expected to inhibit cell proliferation.

SUMMARY OF THE INVENTION

The invention is based on the discovery that non-psychoactive THC derivatives, such as THC acids, can decrease cell proliferation. Moreover, this effect is not dependent on an increase in the rate of apoptosis, which has been identified as a CB1 receptor-mediated activity of THC (Sanchez et al., FEBS Lett. 436:6–10, 1998).

Accordingly, the invention features a method of decreasing cell proliferation in a mammal (e.g., a human) by identifying a mammal in which a decrease in cell proliferation is desirable, and administering to the mammal an amount of a compound of Formula I effective to decrease cell proliferation in the mammal,

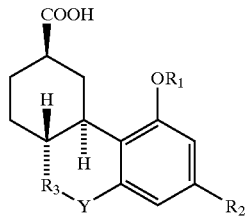

where $R^1$ is a hydrogen atom, —$COCH_3$, or —$COCH_2CH_3$; and $R^2$ is a branched $C_5$–$C_{12}$ alkyl. $R^1$ can be hydrogen, and $R^2$ can be a $C^9$ alkyl, which can be a branched alkyl such as 1,1-dimethylheptyl.

The invention also features a method of decreasing cell proliferation in a mammal (e.g., a human) by identifying a mammal in which a decrease in cell proliferation is desirable, and administering to the mammal an amount of a compound of Formula II effective to decrease cell proliferation in the mammal,

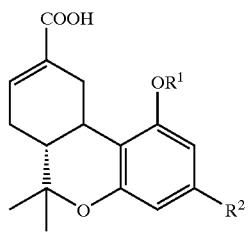

wherein $R_1$ is hydrogen, —$COCH_3$, or —$COCH_2CH_3$; $R_2$ is a branched $C_{5-12}$ alkyl compound which may have a terminal aromatic ring, or a branched —$OCHCH_3(CH_2)_m$, alkyl compound which may have a terminal aromatic ring, wherein m is 0 to 7; $R_3$ is hydrogen, a $C_{1-8}$ alkyl compound, or a $C_{1-8}$ alkanol compound; and Y is nil or a bridging group of NH or oxygen; provided that where Y is oxygen and $R_2$ is a branched $C_{5-12}$ alkyl compound, $R_3$ is not —$CHCH_3$.

Preferred compounds of Formula II are obtained when R1 is hydrogen, R2 is 1',1'-dimethylheptyl, and Y is nil. Thus, in this preferred form, the compounds have Formula III below:

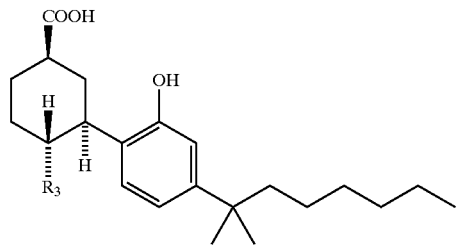

In these compounds, R includes hydrogen; branched or unbranched $C_{1-8}$ alkyl compounds, and branched or unbranched $C_{1-8}$ alkanol compounds. In another preferred form, R is methyl or methanol, or a branched or unbranched ethyl, propyl, ethanol, or propanol.

The compounds may be administered orally (e.g., as a dietary supplement), systemically, intravenously, or via an implant, which can provide slow release of the compound. In addition, the compound can be administered for treatment of a pre-existing disease or condition that is characterized by cell proliferation, or for prophylaxis against such a disease or condition. The compounds can be administered to the mammal at a dose of about 0.1 to 20 mg/kg body weight (e.g., about 0.2 to 2 mg/kg body weight) to effectively decrease cell proliferation. The method is particularly useful in treating a mammal that is suffering from cancer.

In addition, a cell in vitro can be contacted with the compounds to decrease or abolish the cell's ability to proliferate.

As used herein, "cell proliferation" means an increase in cell number. By "decreasing cell proliferation" is meant a decrease in cell proliferation that is not solely due to an increase in apoptosis.

As used herein, "alkyl" means a straight or branched hydrocarbon chain containing carbon atoms or cyclic hydrocarbon moieties. These alkyl groups may also contain one or more double bonds or triple bonds. By "substituted alkyl" is meant an alkyl in which an atom of the alkyl is substituted with an atom, e.g., a sulfur, oxygen, or halogen atom.

The methods of the invention provide a new use for non-psychoactive cannabinoids as drugs for the treatment or prophylaxis of a condition or disease characterized by cell proliferations (e.g., cancer). Because of the low toxicity, non-psychoactive nature, and low abuse potential of such cannabinoids, the compounds can be used as a dietary supplement (e.g., like a daily vitamin pill) to prevent cancer. In addition, the compounds can be applied topically, e.g., to a skin lesion characterized by undesirable cell proliferation, such as in psoriasis.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 3 is a line graph of concentration of various compounds versus neutral lipids per million cells.

FIG. 4 is a line graph of days post-inoculation versus tumor diameter.

DETAILED DESCRIPTION

Figure 1:
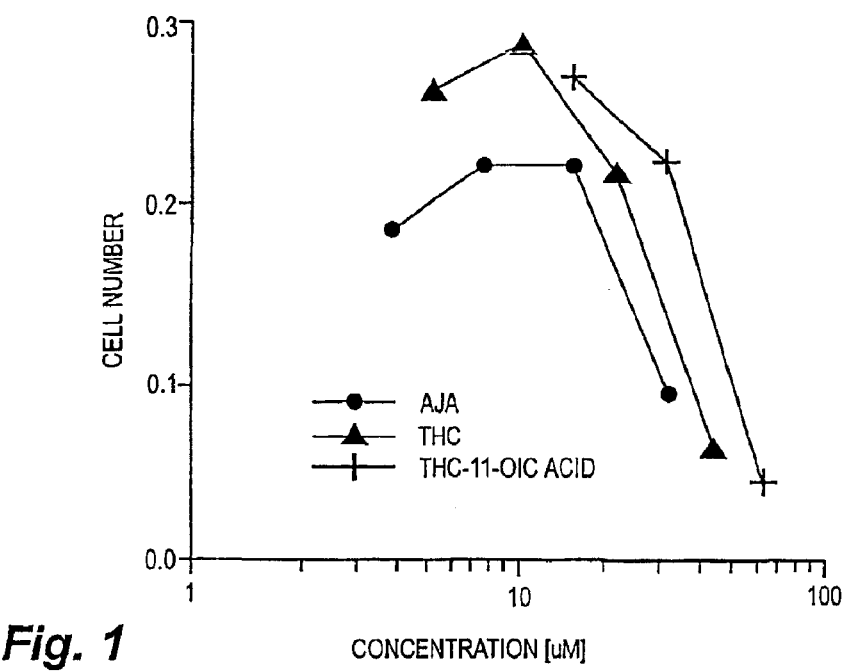
FIG. 1 is a line graph of concentration of various compounds versus cell number.

The invention relates to methods of decreasing cell proliferation (e.g., cancer treatment) in a mammal by administering a THC derivative to the mammal. These THC derivatives (e.g., the compounds defined by Formulas I, II and III) have reduced or no psychoactivity and do not bind to the CB1 receptor. Such THC derivatives are known and can be synthesized (see, e.g., U.S. Pat. No. 5,338,753: Burstein et al., J. Medicinal Chem. 35:3185–3141, 1992; and Burstein, Pharmacol. Ther. 82:87–96, 1999).

The THC derivative can be administered via any appropriate route, e.g. intravenously, intraarterially, topically, by injection, intraperitoneally, intrapleurally, orally, subcutaneously, intramuscularly, sublingually, intraepidermally, or rectally. It can be formulated as a solution, suspension, suppository, tablet, granules, powder, capsules, ointment, or cream. In the preparation of these pharmaceuticals, a solvent (e.g., water or physiological saline), solubilizing agent (e.g., ethanol, Polysorbates, or Cremophor EL7), agent for making isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils) can be added. If necessary, glycerin, dimethylacetamide, 70% sodium lactate, a surfactant, or a basic substance such as sodium hydroxide, ethylenediamine, ethanolamine, sodium bicarbonate, arginine, meglumine, or trisaminomethane is added. Pharmaceutical preparations such as solutions, tablets granules or capsules can be formed with these components. Compositions for slow release of the compound can be formed as described in U.S. Pat. No. 4,880,830.

The dose of the compounds of the present invention is determined in consideration of the results of animal experiments and various conditions. More specific doses obviously vary depending on the administration method, the condition of the subject such as age, body weight, sex, sensitivity, food eaten, dosage intervals, medicines administered in combination, and the source, seriousness, and degree of the affliction. The optimal dose and the administration frequency under a given condition must be determined by the appropriate dosage test of a medical specialist based on the aforementioned guide.

Before administration into humans, THC derivatives can be tested for biological activity (i.e., ability to decrease cell proliferation) both in vitro or in vivo. In vitro testing can be performed as described in the example below, a well as described in Marshall et al., Growth Reg. 5:69–84, 1995. In vivo animal models for tumor growth are well known, such as described in Nagane et al., Cancer Res. 60:847–53, 2000; and Price et al., Clin. Cancer Res. 5:845–54, 1999.

The invention will be farther described in the following example, which does not limit the scope of the invention defined by the claims. The example below illustrates the use of 1',1'-dimethylheptyl-$\Delta^8$-THC-11-oic acid (also known as CT3 and ajulemic acid) in decreasing cell proliferation.

EXAMPLE

Materials and Methods

Cells and materials. C6 glioma and U87 glioma cells were obtained from ATCC (Manassas, Va.). Other human lines were harvested and maintained in the Cancer Center Tumor Bank. WI38 cells were obtained from the Tissue Culture Facility of the University of Massachusetts Medical Center (Worcester, Mass.). All chemicals and solvents were obtained from Sigma-Aldrich (St. Louis, Mo.) unless indicated otherwise. THC and THC-11-oic acid were supplied by NIDA. Ajulemic acid was synthesized as described in Burstein et al., J. Medicinal Chem. 35:3185–3141, 1992.

Cell proliferation assays. In vitro changes in the number of cells were measured using the MTT assay as described in Marshall et al., Growth Reg. 5:69–84, 1995.

Flow cytometry/cell cycle analysis. For flow cytometry, cells were grown in low serum (0.5%) for two days to synchronize cells in G0/G1, after which they were placed in high serum (10%) for two days. The cells were then labeled with propidium iodide and fixed in 4% paraformaldehyde. Cells were examined using a MoFlo Facs sorter for DNA content.

Lipid incorporation assay. Cells were treated as follows. Monolayers of C-6 cells were prepared in 24 well culture dishes as described above. Carboxy labelled $^{14}$C-arachidonic acid (150,000 dpm/well) obtained from ARC, St. Louis. Mo. (specific activity of 55 mCi/mmol) was added to each monolayer and incubated for 2 hours. Treatment with the indicated cannabinoid was initiated by the addition of the drug in 10 $\mu$l of DMSO to 1 ml of the culture medium covering each monolayer. Treatment was continued for 48 hours, except as indicated otherwise. After this incubation, the media were removed and discarded. After washing twice, each time with 1 ml PBS, the cellular lipids were extracted for 1 hour with 0.5 ml of absolute ethanol at room temperature. All treatments were performed in quadruplicate. Controls cells were treated identically, except that no cannabinoid was present.

To perform group analysis of the extracted lipids, the lipid samples were lyophilized. Prior to evaporation under vacuum, $^{14}$C-cholesterol (50,000 dpm) was added as a recovery marker (ARC, St. Louis Mo.; specific activity of 50 mCi/mmol). The sample residues were then dissolved in 30 µl of methanol containing 10 µg each of steroyl-arachidonoyl diglyceride, triolein, and lecithin and applied to 0.25 mm silica gel thin layer plates. A first elution was performed using a 9:1 mixture of dichloromethane:acetone for analysis of neutral lipids. The Rf values of the standards were as follows: lecithin=0, cholesterol=0.38, diglyceride=0.64, and triglyceride=0.81. Following the quantitation of the neutral lipids, a second elution was carried out using a 50:25:8:4 mixture of chloroform:methanol:acetic acid:water as the eluent for the analysis of phospholipids. The Rf value of lecithin was 0.33. DG and TG moved to the solvent front. All standards were detected by exposure to iodine vapor.

Labelled lipids were quantitated as follows. The zones of radioactivity were detected by exposure of the plates to X-ray film for 48 hours. A TIFF computer file of the fim was generated using the Fluor-S System (Biorad). The chromatograms were quantified using NIH Image software. Peak height values of the display were used, since all labelled components resided in narrow, sharp peaks on the chromatograms. Each component value was adjusted for recovery using the individual cholesterol standard values for each zone. The values obtained were then divided by the numbers of cells in each well and the results expressed as an index per million cells.

Protein kinase C (PKC) assay. Cells were transferred into MEM media (0.5% serum) and cultured overnight. The next day, cells were treated with either DMSO or 25 µM ajulemic acid for the specified incubation time, after which the plates were trypsinized. $5 \times 10^6$ trypsinized cells were assayed for PKC activity using a kit (Calbiochem, cat. no. 53984).

In vivo subcutaneous model. $10^6$ U87 cells were injected into the right flank muscle of male nu/nu BALBc mice (Charles River). Two days after inoculation, the mice received either 0.1 mg/kg ajulemic acid in 0.05 ml of safflower oil or 0.05 ml safflower oil by oral administration. Thereafter, identical dosings were performed on each Monday, Wednesday, and Friday. When visible tumors appeared, the size of the tumors were estimated by averaging the values of two roughly perpendicular diameters measurements. Visible tumors were measured on the days of drug administration.

Results

Using the MTT assay to assess growth potential it was noted that $\Delta^9$-THC, THC-11-oic acid and ajulemic acid all inhibited C6 glioma cells in a dose dependent fashion with $IC_{50}$ values of 10, 20 and 55 µM, respectively (FIG. 1). The proliferation of a number of human cell lines derived from a variety of cancer types (brain, breast, bladder, lung, and prostate) was tested for sensitivity to 25 µM of each agent for 48 hours. At this dosage, ajulemic acid inhibited cell proliferation better than either THC or THC-11-oic acid. (As used herein, "THC" refers to $\Delta^8$- or $\Delta^9$-THC.) The inhibition levels were 61.3±12.1, 39.4±22.0, and 13.1±18.5% (mean±SD) for ajulemic acid, THC, and THC-11-oic acid, respectively, with p<0.001 in a one-way ANOVA, pairwise multiple comparison (Student-Newman-Keuls method), as shown in Table 1.

TABLE 1

Percent inhibition of human cancer cell line growth in 48 hour MTT assay

| Line | Tissue of Origin | $\Delta^9$-THC (25 µM) | Ajulemic Acid (25 µM) | THC-11-oic acid (25 µM) |
|---|---|---|---|---|
| U87 | Brain | 20 ± 5 | 54 ± 2 | 5 ± 1 |
| U373 | Brain | 0 | 34 ± 1 | 0 |
| U118 | Brain | 39 ± 5 | 60 ± 2 | 14 ± 3 |
| A172 | Brain | 42 ± 5 | 76 ± 1 | 61 ± 2 |
| HS578T | Breast | 52 ± 5 | 60 ± 2 | 2 ± 1 |
| HT1376 | Bladder | 23 ± 5 | 60 ± 2 | 21 ± 12 |
| J82 | Bladder | 63 ± 6 | 57 ± 3 | 1 ± 1 |
| Calu6 | Lung | 28 ± 5 | 69 ± 3 | 19 ± 5 |
| Du145 | Prostate | 55 ± 7 | 74 ± 2 | 7 ± 3 |
| PC3 | Prostate | 72 ± 2 | 69 ± 2 | 1 ± 1 |

Compared to THC, ajulemic acid was significantly more effective (p<0.05) at this dosage in six of the ten lines tested.

The three cannabinoids also inhibited the normal rat fibroblast cell line WI38. However, it was notable that, unlike THC, ajulemic acid inhibited the proliferation of WI38 cells less than the proliferation of C6 glioma cells. For example, in three different experiments at the 25 µM dosage, $\Delta^9$-THC inhibited WI38 cell proliferation 66%, in comparison to 50% for the C6 cells. By contract, incubation with ajulemic acid for two days resulted in an opposite effect. Thus, there was a 65% inhibition for C6 compared to 44% for WI38 cells. The data suggests that ajulemic acid was more toxic to tumor than to normal cells.

Figure 2:
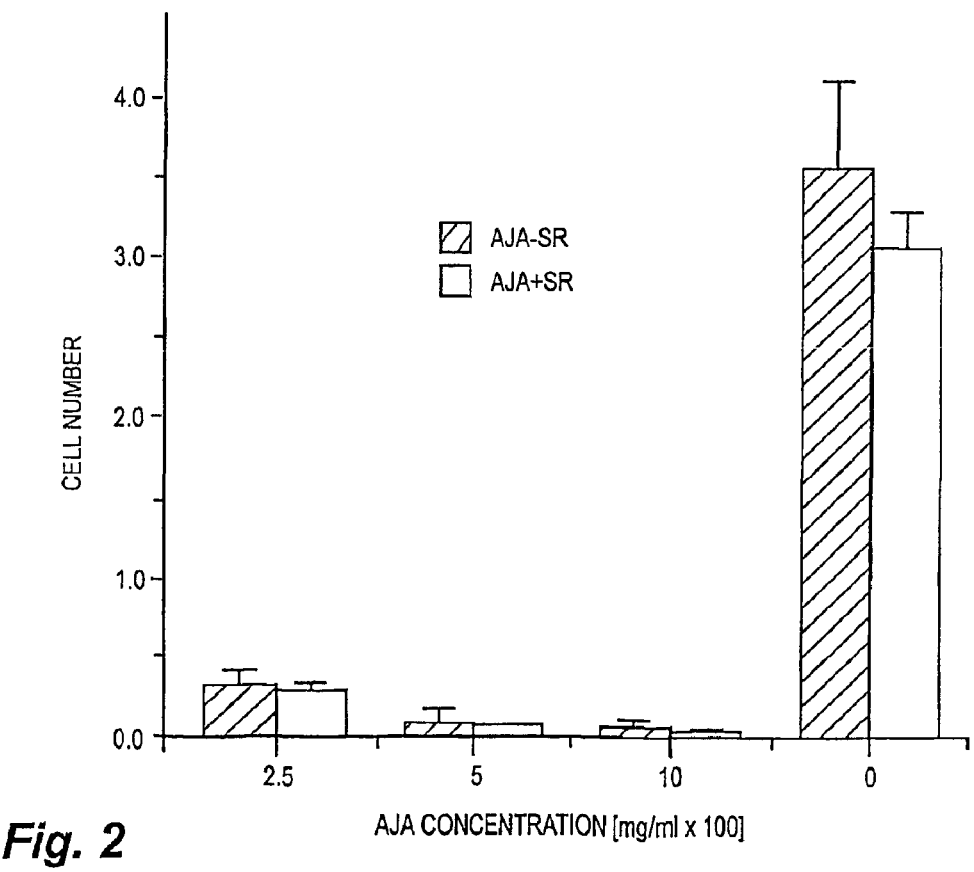
FIG. 2 is a bar graph of ajulemic acid concentration versus cell number.

To assess whether ajulemic acid's effect was receptor-mediated, a preparation 95% enriched in the D-isomer of ajulemic acid was used to examine the stereospecificity of the effect observed above. There was a marked decrease in the potency of a 25 µM dose of the D-isomer compared to the L-isomer of ajulemic acid (p<0.001, t-test) (FIG. 2). This result supported the contention that ajulemic acid's activity was stereospecific and therefore most likely receptor-mediated.

Three features of ajulemic acid's effect on tumor cells suggested that this effect was mediated by a mechanism distinct from that of $\Delta^9$-THC. First, the compound's inhibition of cell proliferation was not reversible with a CB1 antagonist. Co-incubation of C6 glioma cells with 3.2 µM of a specific antagonist resulted in a 150% decrease in the potency of THC, compared to a slight potentiation of ajulemic acid's effect (FIG. 3). This result indicates that a large component of THC's antitumor effect is CB1 receptor-mediated, while ajulemic acid's were not.

Second, ajulemic acid's antitumor activity was associated with a marked increase in cell size after 48 hours of exposure to the compound. In order to investigate this effect further, the effect of ajulemic acid on cell cycle kinetics was assessed. C6 glioma cells were incubated for 24 hours in media containing 0.5% serum to synchronize them in G1/G0. The cells were then exposed to media containing 10% serum either with or without 25 µM ajulemic acid for two days. As shown in Table 2, an increased number of treated cells was seen in both S (from 4.4% to 13.0% p=0.003, t-test) and G2/M (from 21.9% to 32.3%, p=0.005, t-test) phases of the cell cycle, suggesting that treated cells could synthesize DNA but were not able to complete mitosis. Importantly, the rate of apoptosis (as assessed by the lack of sub-G0 cells in both control and treated cells) was not increased.

TABLE 2

Cell cycle analysis of Control and AJA-treated C6 glioma cells

| | G0/G1 (mean % ± SD) | S (mean % ± SD) | G2/M (mean % ± SD) |
|---|---|---|---|
| Control | 46.3 ± 3.6 | 4.4 ± 0.3 | 21.9 ± 1.1 |
| AJA-treated | 39.1 ± 1.3* | 13.0 ± 2.3** | 32.3 ± 3.0*** |

*p < 0.02,
**p = 0.003,
***p = 0.005, all determined by t-test.

Third, another distinctive feature of ajulemic acid's antitumor effect was the appearance of refractile bodies that could be easily visualized with phase microscopy. Both the number of cells that had retractile bodies as well as the number of refractile bodies/cell increased over time. After 48 hours, 83% of ajulemic acid-treated C6 cells had one or more refractile bodies compared to 27% to THC-treated cells (p<0.001, Chi-square analysis). The mean number of refractile bodies per cell was also much higher for ajulemic acid-treated cells compared to THC-treated cells (1.78±1.6 vs. 0.22±0.5 per cell, p<0.001, t-test). Interestingly, no refractile bodies were noted in either WI38 cells treated for this length of time at this dosage of ajulemic acid or in C6 glioma cells treated with 25 $\mu$M THC-11-oic acid.

To further explore the nature of the cell enlargement and refractile bodies, cells were examined under electron microscopy. Ajulemic acid-treated cells were neither apoptotic nor necrotic. In fact, these cells appeared metabolically active. This is consistent with additional observations that, although cell proliferation was markedly inhibited by ajulemic acid, the treated cells have a high (>95%) viability rate as assessed by trypan blue exclusion and recover quickly upon drug removal. Moreover, ajulemic acid-treated cells were enlarged and contained large lipid droplets, the identity of which was confirmed by bleaching with osmium tetrachloride.

To investigate the source of the increased lipid content, C6 cells were grown and treated with 25 $\mu$M dose of cannabinoid in the presence of $^{14}$C-labeled arachidonic acid. Compared to cells treated with vehicle (no cannabinoid), THC, or THC-11-oic acid, a significant increase above basal levels was only noted for ajulemic acid (p<0.05, Duniiett's test of multiple comparisons versus control) after 48 hours of incubation (FIG. 3). At this dose of ajulemic acid, the content of both tri-and di-glyceride was over three-fold greater than in controls. By contrast, no significant increase in the level of phosphatidylcholine for any of the cannabinoid treatments was detected. A similar result was seen after incubation with a $^{14}$C-oleic acid label.

Because diacyl glycerol (DAG) is an important signal transducer of protein kinase C, the effect of ajulemic acid treatment on the PKC activity in C6 cells was examined. After exposure to ajulemic acid, PKC activity increased within five minutes and remained approximately two-fold above that of control for one hour, suggesting that PKC plays a role in ajulemic acid-mediated inhibition of cell proliferation. At least two alternative explanations for this observation exist: (1) the PKC isozymes that were stimulated were those with slow growth, such as PKCδ; and (2) the increased DAG was modulating some other downstream mediator, such as β-chimaerin, to a greater extent such that the balance is towards anti-proliferation.

Whether ajulemic acid has in vivo antitumor activity was determined using a nude mouse tumor model. The growth of the human glioma cell line U87 injected subcutaneously in nude mice was assessed with and without ajulemic acid administration. For these experiments, ajulemic acid treatment was initiated two days after inoculation of $10^6$ tumor cells in the mice. A delay in both the appearance and size of tumors were seen for the group receiving 0.1 mg/kg ajulemic acid thrice weekly (FIG. 4). At day 25 post-inoculation, 5 of 5 control mice had tumors with a mean diameter of 16.3±3.2 mm, while the mean diameter in the treated group was 3.8±8.5 mm (n=5, p–0.015, t-test). These in vivo results confirm the ability of ajulemic acid to inhibit cell proliferation, in this case in a tumor.

What is claimed is:

1. A method for decreasing cell proliferation in a mammal, the method comprising the steps of identifying a mammal in which a decrease in cell proliferation is desirable; and administering to the mammal, in an amount effective to decrease cell proliferation in the mammal, a compound having the formula

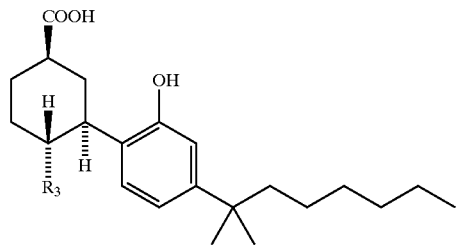

wherein $R_3$ is hydrogen, a branched or unbranched $C_{1-8}$ alkyl compound, a branched or unbranched $C_{1-8}$ alkanol compound, methyl, a branched or unbranched ethyl, a propyl group, methanol, ethanol, or propanol; and with the proviso that when said cell proliferation is associated with cancer, the cancer is selected from the group consisting of brain cancer, breast cancer, bladder cancer, lung cancer and prostate cancer.

2. The method of claim 1, wherein $R_3$ is hydrogen, branched or unbranched $C_{1-8}$ alkyl compounds, and branched or unbranched $C_{1-8}$ alkanol compounds.

3. The method of claim 1, wherein $R_3$ is methyl or methanol, or a branched or unbranched ethyl, propyl, ethanol, or propanol.

4. The method of claim 1, wherein the mammal is human.

5. The method of claim 1, wherein the compound is administered orally.

6. The method of claim 1, wherein the compound is administered systemically.

7. The method of claim 1, wherein the compound is administered via an implant.

8. The method of claim 7, wherein the implant provides slow release of the compound.

9. The method of claim 1, wherein the compound is administered intravenously.

10. The method of claim 1, wherein the compound is administered topically.

11. The method of claim 1, wherein the cell proliferation is associated with cancer.

12. The method of claim 1, wherein the amount of the compound administered is about 0.1 to 20 mg/kg body weight of the mammal.

13. The method of claim 1, wherein the amount of the compound administered is about 0.2 to 2 mg/kg body weight of the mammal.

* * * * *

UNITED STATES PATENT AND TRADEMARK OFFICE
CERTIFICATE OF CORRECTION

PATENT NO.        : 6,974,835 B2                                                Page 1 of 1
APPLICATION NO.   : 10/276818
DATED             : December 13, 2005
INVENTOR(S)       : Burstein et al.

It is certified that error appears in the above-identified patent and that said Letters Patent is hereby corrected as shown below:

Title page, Item 75 after Inventors:    Delete the following names and addresses
~~Lawrence Recht, Holden, MA (US)~~
~~Robert B. Zurier, Princeton, MA (US)~~

Signed and Sealed this

Third Day of June, 2008

JON W. DUDAS
*Director of the United States Patent and Trademark Office*